United States Patent
Hazel et al.

(10) Patent No.: US 8,624,054 B2
(45) Date of Patent: Jan. 7, 2014

(54) CARBONYLATION PROCESS FOR THE PRODUCTION OF METHYL ACETATE

(75) Inventors: Nicholas John Hazel, Beverley (GB); Lesley Ann Key, Hull (GB); Mark Stephen Roberts, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 364 days.

(21) Appl. No.: 12/998,742

(22) PCT Filed: Nov. 19, 2009

(86) PCT No.: PCT/GB2009/002696
§ 371 (c)(1),
(2), (4) Date: Jul. 5, 2011

(87) PCT Pub. No.: WO2010/061169
PCT Pub. Date: Jun. 3, 2010

(65) Prior Publication Data
US 2011/0319654 A1     Dec. 29, 2011

(30) Foreign Application Priority Data

Nov. 27, 2008  (EP) ..................... 08253827

(51) Int. Cl.
C07C 67/36 (2006.01)
C07C 51/10 (2006.01)
C07C 67/37 (2006.01)
C07C 69/14 (2006.01)

(52) U.S. Cl.
USPC ............ 560/232; 560/129; 562/517; 562/519

(58) Field of Classification Search
None
See application file for complete search history.

(56) References Cited

U.S. PATENT DOCUMENTS

2006/0252959 A1   11/2006   Cheung et al.
2006/0287551 A1*  12/2006   Cheung et al. ............... 560/232

FOREIGN PATENT DOCUMENTS

| EP | 0 596 632 | 5/1994 |
| EP | 2 000 433 | 12/2008 |
| EP | 2 085 375 | 8/2009 |
| WO | WO 01/07393 | 2/2001 |
| WO | WO 2005/105720 | 11/2005 |

OTHER PUBLICATIONS

International Search Report for PCT/GB2009/00002696, mailed Jan. 27, 2010.
Written Opinion of the International Searching Authority for PCT/GB2009/00002696, mailed Jan. 27, 2010.
Cheung, P. et al., "Selective Carbonylation of Dimethyl Ether to Methyl Acetate Catalyzed by Acidic Zeolites", Angew. Chem. Int. Ed., vol. 45, (2006), pp. 1617-1620.
Tartamella, T.L. et al., "Role of Acid Catalysis in Dimethyl Ether Conversion Processes", Proceedings of the Annual International Pittsburgh Coal Conference, vol. 2, (Jan. 1, 1996), pp. 996-1001.
PCT Notification Concerning Transmittal of International Preliminary Report on Patentability; Form PCT/IB/326, International Application No. PCT/GB2009/002696, filed Nov. 19, 2009 (6 pgs).

* cited by examiner

*Primary Examiner* — Johann R Richter
*Assistant Examiner* — Mark Luderer
(74) *Attorney, Agent, or Firm* — Nixon & Vanderhye

(57) ABSTRACT

A process for the production of methyl acetate by reacting dimethyl ether with carbon monoxide into a carbonylation reactor containing a mordenite catalyst in the presence of added methyl acetate and/or acetic acid.

17 Claims, 5 Drawing Sheets

CARBONYLATION PROCESS FOR THE PRODUCTION OF METHYL ACETATE

Figure 1:
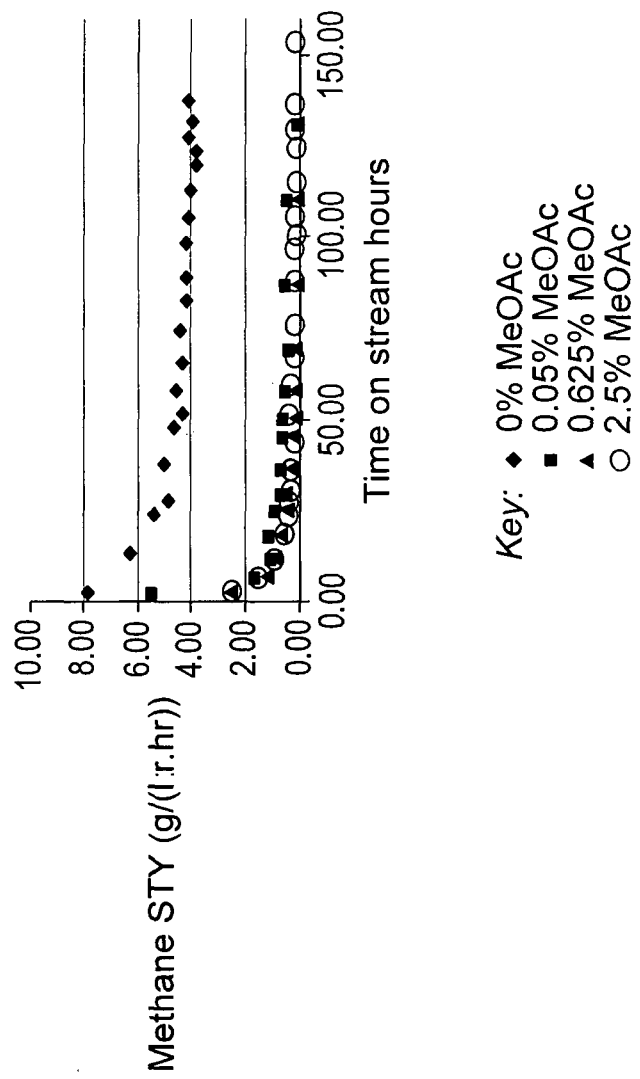

This application is the U.S. national phase of International Application No. PCT/GB2009/002696, filed 19 Nov. 2009, which designated the U.S., and claims priority to EP Application No. 08253827.3, filed 27 Nov. 2008, the entire contents of each of which are hereby incorporated by reference.

This invention relates to a carbonylation process for the production of methyl acetate by reacting dimethyl ether with carbon monoxide in the presence of added methyl acetate and/or acetic acid and a mordenite catalyst.

Liquid phase carbonylation processes such as the carbonylation of methanol and/or reactive derivatives thereof in the presence of homogeneous catalysts to produce acetic acid are operated commercially. Gas phase carbonylation processes employing methanol and dimethyl ether using heterogeneous catalysts are also known.

EP-A-0 596 632 describes a vapour phase process for the carbonylation of methanol to produce acetic acid at high temperatures and pressures in the presence of a mordenite catalyst which has been loaded with copper, nickel, iridium, rhodium or cobalt WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof.

WO 2005/105720 describes a process for production of a carboxylic acid and/or an ester or anhydride thereof by carbonylating an aliphatic alcohol or reactive derivative thereof with carbon monoxide in the substantial absence of halogens at a temperature in the range 250-600° C. and a pressure in the range 10 to 200 bar in the presence of a mordenite catalyst which has been modified with copper, nickel, iridium, rhodium or cobalt and has as framework elements, silicon, aluminium, and at least one of gallium, boron and iron.

WO 2006/121778 describes a process for the production of a lower alkyl ester of a lower aliphatic carboxylic acid by carbonylating under substantially anhydrous conditions a lower alkyl ether, such as dimethyl ether, with carbon monoxide in the presence of a mordenite or ferrierite catalyst.

A disadvantage of conducting carbonylation reactions in the presence of a zeolite catalyst such as a mordenite is that selectivity to the carbonylation product methyl acetate is decreased owing to the formation of by-products, and, in particular to the formation of the by-products, methane and $C_{2+}$ hydrocarbons. The $C_{2+}$ hydrocarbons are typically, $C_2$ to $C_6$ aliphatic hydrocarbons, such as ethane and propane, $C_2$ to $C_6$ alkenes, such as ethylene and propylene. Aromatic hydrocarbons may also be formed, such as methylated benzenes, for example, xylenes.

Thus, it would be advantageous if such by-product formation in mordenite catalysed carbonylation processes to produce methyl acetate could be reduced.

It has now been found that if the carbonylation reaction is conducted in the presence of added methyl acetate (that is, methyl acetate which is in addition to that produced as a product of the carbonylation reaction between dimethyl ether and carbon monoxide) and/or acetic acid, the formation of by-products is reduced.

Accordingly, the present invention provides a process for the production of methyl acetate, which process comprises carbonylating dimethyl ether with carbon monoxide in one or more carbonylation reaction zones in the presence of a mordenite catalyst to produce methyl acetate product characterised in that at least one of methyl acetate and acetic acid is added to at least one of said reaction zone(s).

Advantageously, it has been found that if at least one of methyl acetate and acetic acid is fed to the carbonylation process, the formation of by-products, and, in particular the formation of methane and $C_{2+}$ hydrocarbons by-products is reduced.

Furthermore, if methyl acetate is present in the dimethyl ether feed introduced into a reaction zone on start-up of the carbonylation reaction, it has been found that hydrocarbon formation is significantly suppressed, thereby allowing an improved reaction start-up to be achieved.

Thus, the present invention further provides for the use of at least one of methyl acetate and acetic acid in a carbonylation process to reduce the formation of by-products, wherein said process comprises carbonylating dimethyl ether with carbon monoxide in one or more carbonylation reaction zone(s) in the presence of a mordenite catalyst to produce methyl acetate product, characterised in that at least one of methyl acetate and acetic acid is added to at least one of said reaction zone(s).

The process of the present invention is a carbonylation process in which dimethyl ether is carbonylated with carbon monoxide to produce methyl acetate. The dimethyl ether may be substantially pure or may contain small quantities of inert impurities. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. In the process of the present invention the dimethyl ether feed may additionally comprise small amounts of methanol provided that the amount of methanol present in the feed is not so great as to inhibit the carbonylation reaction to methyl acetate product. It has been found that 5 wt % or less, such as 1 wt % or less of methanol may be tolerated in the dimethyl ether feed.

Dimethyl ether may also be generated from dimethyl carbonate, for example, by contacting liquid dimethyl carbonate with gamma-alumina to decompose the dimethyl carbonate to dimethyl ether and carbon dioxide.

Suitably, dimethyl ether is introduced into a reaction zone at a concentration in the range of at least 1.0 mol % to 20 mol %, for example, 1.5 mol % to 10 mol %, such as 2.5 to 5 mol %, based on the total gaseous feeds (including recycles) to the reaction zone. Where more than one reaction zone is employed, the concentration of dimethyl ether introduced into each reaction zone can be the same or different. The dimethyl ether introduced into a reaction zone may be fresh and/or recycle dimethyl ether.

In addition to dimethyl ether and carbon monoxide, the gaseous feeds to a reaction zone may include methyl acetate, acetic acid, hydrogen and inert gases, such as nitrogen, helium and argon.

In the process of the present invention, at least one of methyl acetate and acetic acid is added to at least one reaction zone. Where more than one reaction zone is employed, methyl acetate and/or acetic acid may be added to some but not necessarily all of the reaction zones employed.

Where methyl acetate is added to a reaction zone, the molar ratio of methyl acetate to dimethyl ether is suitably, in the range 1:100 to 5:1, such as 1:10 to 3:1.

Suitably, methyl acetate may be added to a reaction zone in an amount of 5 mol % or less, based on the total gaseous feeds (including recycles). Preferably, methyl acetate is added in an amount in the range 0.05 mol % to 5 mol %, such as 0.5 to 5 mol % based on the total gaseous feeds (including recycles).

Suitably, where dimethyl ether is introduced into a reaction zone in an amount of 5 mol %, methyl acetate is suitably present in an amount of 0.5 to 2.5 mol % based on the total gaseous feeds (including recycles).

Where acetic acid is added, it reacts with dimethyl ether present in a reaction zone to generate methyl acetate and methanol. Suitably, the amount of added acetic acid is in the range (greater than 0) to 1 mol % based on the total gaseous feeds (including recycles), for example, in the range 0.1 to 0.8 mol %.

The components of the carbonylation process may be fed separately to a reaction zone or may be fed as mixtures of 2 or more components. Thus, the methyl acetate and/or acetic acid may be fed separately to, or, together with dimethyl ether to a reaction zone.

The methyl acetate may be introduced into a reaction zone as fresh methyl acetate and/or as recycle methyl acetate.

Alternatively or additionally, methyl acetate product from one reaction zone may be added to a successive reaction zone.

The methyl acetate and acetic acid may be fed to a reaction zone as a vapour or they can be fed as a liquid to a pre-vapourisation zone, where they are vaporised prior to contact with the catalyst.

In a preferred embodiment, at least 2 reaction zones connected in series, such as 2 to 30 reaction zones, are employed and dimethyl ether is introduced into one or more of these reaction zones as fresh dimethyl ether together with at least one of fresh and/or recycle methyl acetate and acetic acid.

The carbon monoxide may be substantially pure carbon monoxide, for example, carbon monoxide typically provided by suppliers of industrial gases, or it may contain impurities that do not interfere with the conversion of the dimethyl ether to methyl acetate, such as nitrogen, helium, argon, methane and/or carbon dioxide.

The process of the present invention may be carried out in the presence of hydrogen. Suitably, carbon monoxide and hydrogen may be fed to a reaction zone as a mixture. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1, for example, 1:1 to 4:1.

Where hydrogen is present in the process, it may be present at a partial pressure of at least 0.1 barg, such as 1 to 30 barg.

The molar ratio of carbon monoxide to dimethyl ether is suitably in the range 1:1 to 99:1, such as 2:1 to 60:1.

The catalyst used in the process of the present invention is a mordenite zeolite. The structure of mordenite is well known and defined, for example, in The *Atlas of Zeolite Framework Types* (C. Baerlocher, W. M. Meier, D. H. Olson, 5$^{th}$ ed. Elsevier, Amsterdam, 2001). The web-based version (http://www.iza-structure.org/databases/) is a compendium of topological and structural details about zeolites including mordenite.

Mordenite is commercially available as Na-mordenite, NH$_4$-mordenite or H-mordenite. For use as the catalyst in the carbonylation process of the present invention, mordenite is preferably used in the H-form or ion-exchanged or otherwise loaded with one or more metals.

The ammonium form of mordenite may be converted to the H-form by well-known techniques such as calcination at high temperature. The sodium form of mordenite can be converted to the acid form (H-form) by converting first to the ammonium form by ion exchange with ammonium salts such as ammonium nitrate.

Alternatively, the mordenite may be loaded with at least one metal, preferably selected from copper, silver, gold, nickel, iridium, rhodium, platinum, palladium or cobalt, more preferably, selected from at least one of copper and silver.

The loading of the mordenite with metals may be carried out by any known method such as the well-known techniques of ion-exchange, wet impregnation and incipient wetness. If the mordenite is to be ion-exchanged up to 100% of the cation-exchangable sites on the mordenite may be exchanged with metal ions using well known techniques. It is preferred that any remaining cations in the exchanged mordenite are protons hence it is convenient to start the exchange process from the ammonium or hydrogen form.

As an alternative to ion-exchange, the ammonium or hydrogen form of the mordenite can be impregnated with a solution of metal salts and subsequently dried. If the ammonium form is used, it is preferred to calcine the mordenite after the loading or ion-exchange with the metals has been completed.

The metal loading in the mordenite can be expressed in terms of the fractional loading of the metal as gram atoms of metal per gram atom of aluminium in the mordenite. The metal loading can also be expressed as a mole percentage loading relative to aluminium in the mordenite through the relationship:

mol % Metal=(gram atoms Metal/gram atoms aluminium)×100

Thus, for example, a loading of 0.55 gram atom of copper per aluminium in the mordenite equates to a 55 mol % loading of copper relative to aluminium in the mordenite.

A metal may be loaded in an amount in the range of 1 to 200 mol % relative to aluminium, for example, 50 to 120 mol %, such as 50 to 110 mol % relative to aluminium in the mordenite.

Suitably, the mordenite catalyst for use in the present invention is selected from a H-mordenite, a copper mordenite and a silver mordenite.

For use in the process of the present invention it is preferred that the mordenite has a silica to alumina ratio of at least 5 but, preferably less than or equal to 100, such as in the range 6 to 90, for example 10 to 40.

The process of the present invention is preferably carried out under substantially anhydrous conditions, i.e in the substantial absence of water. The carbonylation of dimethyl ether to methyl acetate does not generate water in-situ. Water has been found to inhibit the carbonylation of dimethyl ether to form methyl acetate. Thus, in the process of the present invention, water is kept as low as is feasible. To accomplish this, the dimethyl ether and carbon monoxide reactants (and mordenite catalyst) are preferably dried prior to introduction into the process. However, small amounts of water may be tolerated without adversely affecting the formation of methyl acetate. Suitably, water may be present in the dimethyl ether feed in an amount of 2.5 wt % or less, such as 0.5 wt % or less.

The process of the present invention may suitably be carried out at a temperature in the range of 100° C. to 350° C.

The process of the present invention may be carried out at a pressure in the range 1 to 100 Barg, such as 10 to 100 barg.

The Gas Hourly Space Velocity (GHSV) is suitably in the range 500 to 40,000 h$^{-1}$, such as 4000 to 10,000 h$^{-1}$.

Because the process of the present invention is preferably carried out in the substantial absence of water, it is preferred that the mordenite catalyst is dried prior to use. The catalyst may be dried, for example by heating to a temperature of 400 to 500° C.

It is preferred that the mordenite catalyst is activated immediately before use by heating the catalyst at elevated temperature for at least one hour under flowing nitrogen, carbon monoxide, hydrogen or mixtures thereof.

Preferably, the process of the present invention is carried out substantially in the absence of halides, such as iodide. By the term 'substantially' is meant that the halide, for example, iodide content of the reactant gases and catalyst is less than 500 ppm, preferably less than 100 ppm.

The process of the present invention is suitably carried out using a fixed bed, fluidised bed or moving bed of the mordenite catalyst.

The process of the present invention may be carried out in a single reaction zone or in at least 2 reaction zones connected in series, such as 2 to 30 reaction zones. One or more reaction zones may be housed in a single reaction vessel. If desired, cooling or additional heating means may be applied between reaction zones.

The primary product of the process of the present invention is methyl acetate but small amounts of acetic acid may also be produced. Methyl acetate product may be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The process may be operated as either a continuous or a batch process, preferably as a continuous process.

In the Figures, FIG. 1 depicts the space time yield (STY) to methane in g/l/h versus time on stream for carbonylation carried out with 0 mol %, 0.05% mol %, 0.625 mol % and 2.5 mol % methyl acetate.

Figure 2:
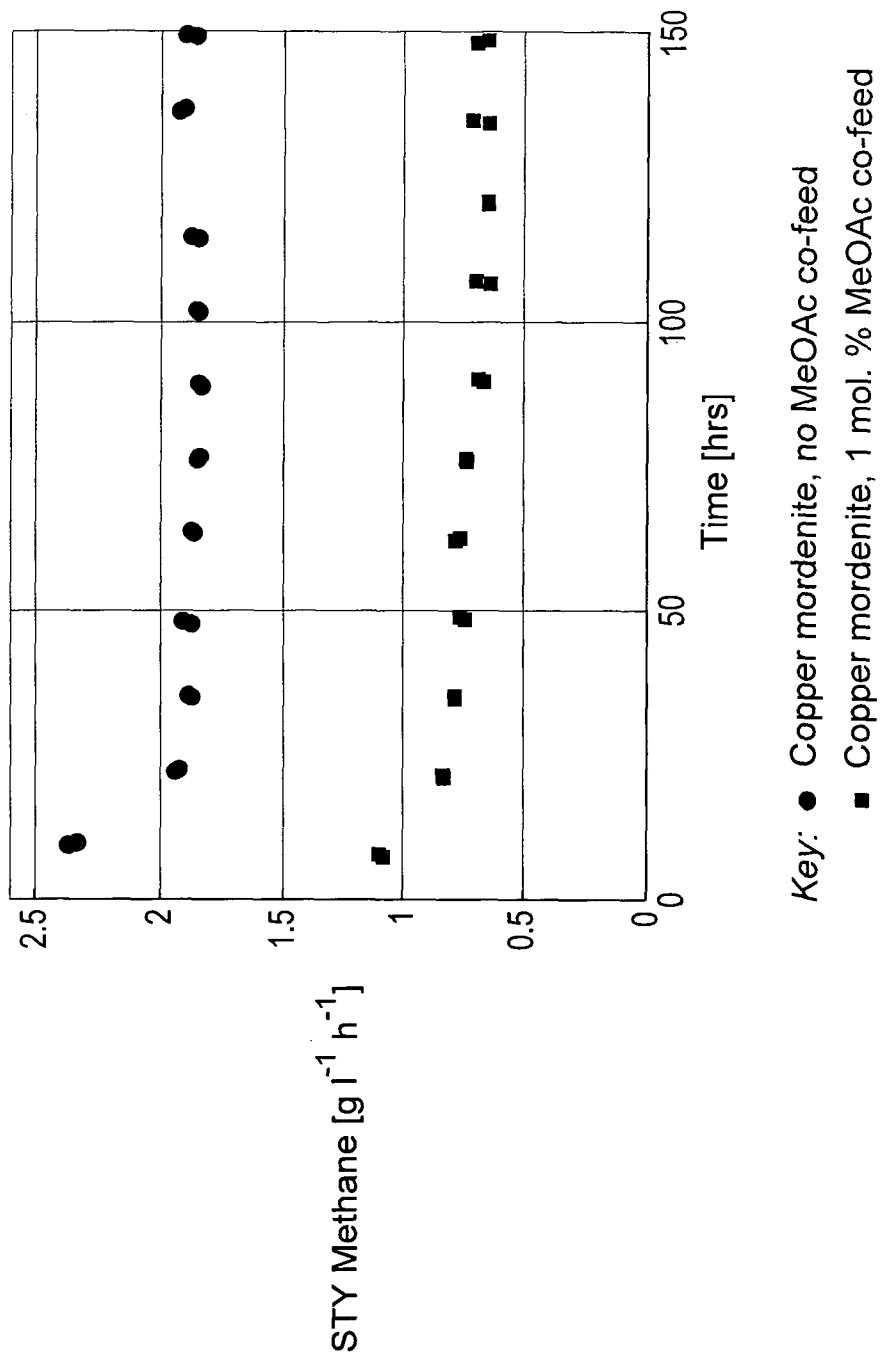

FIG. 2 depicts the space time yield (STY) to methane in g/l/h versus time on stream for carbonylation carried out with 0 mol % and 1 mol % methyl acetate and 2.5 mol % dimethyl ether.

Figure 3:
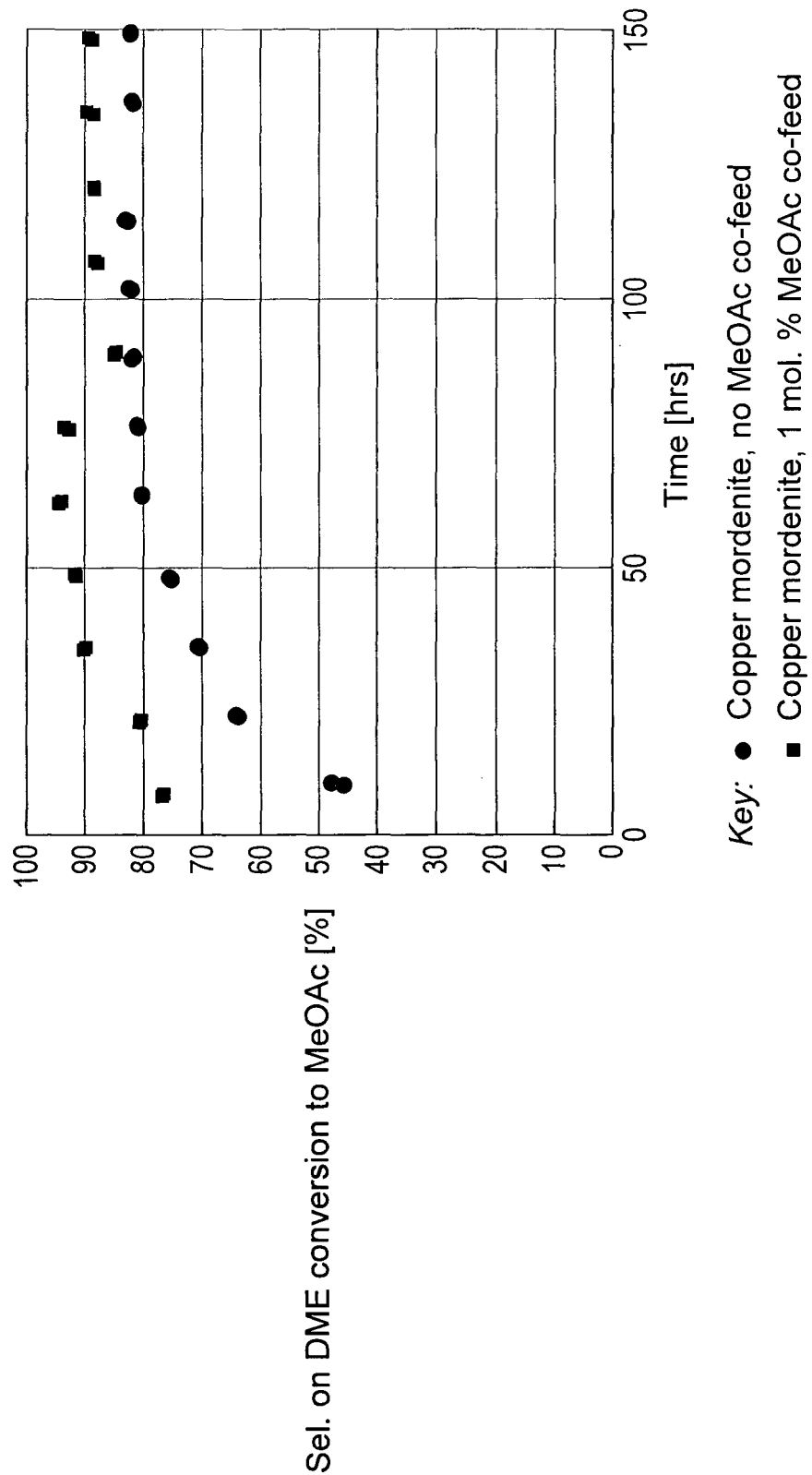

FIG. 3 depicts the selectivity to methyl acetate versus time on stream for carbonylation carried out with 0 mol % and 1 mol % methyl acetate and 2.5 mol % dimethyl ether.

Figure 4:
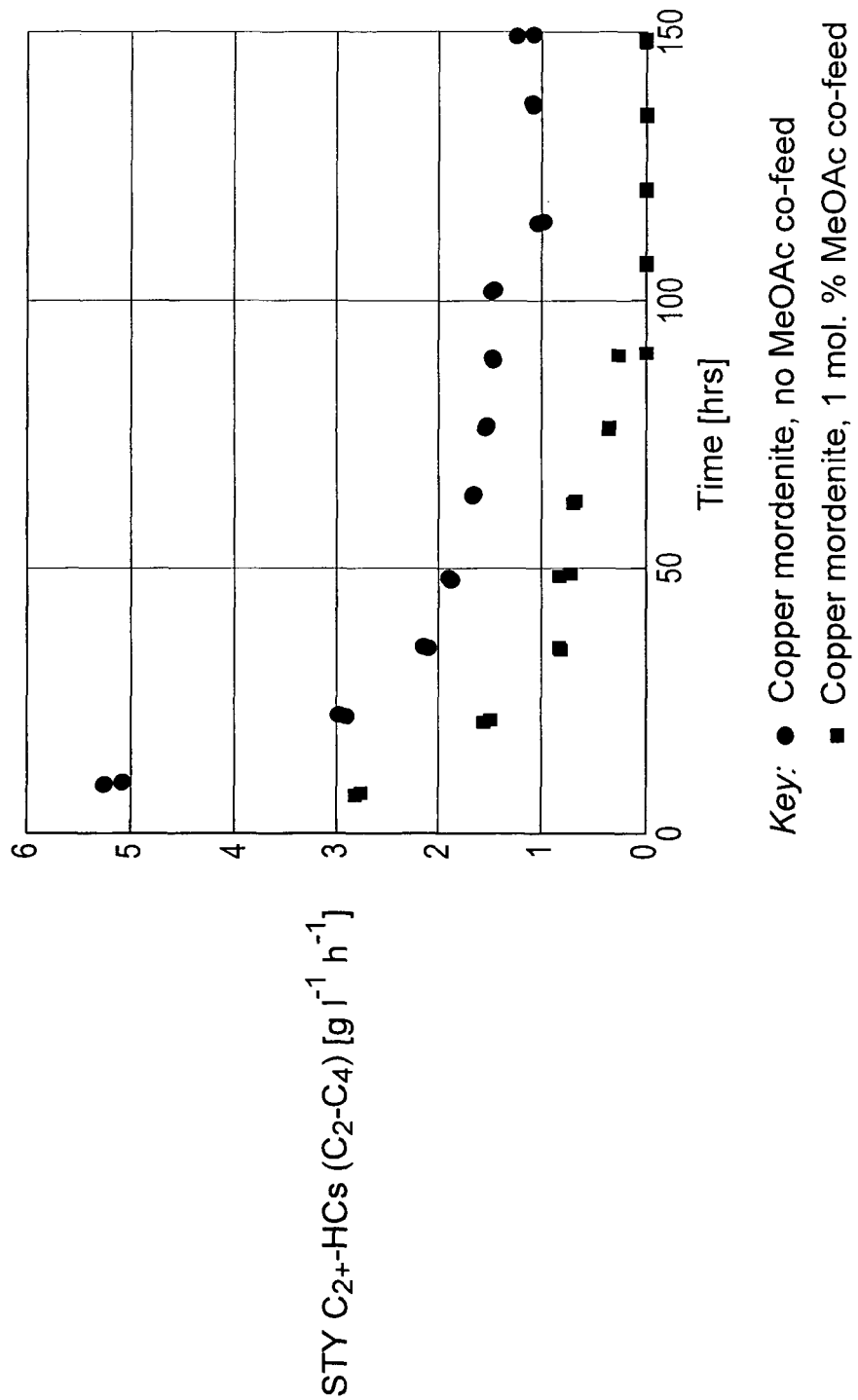

FIG. 4 depicts the space time yield (STY) to $C_{2+}$ hydrocarbons in g/l/h versus time on stream for carbonylation carried out with 0 and 1 mol % methyl acetate and 2.5 mol % dimethyl ether.

Figure 5:
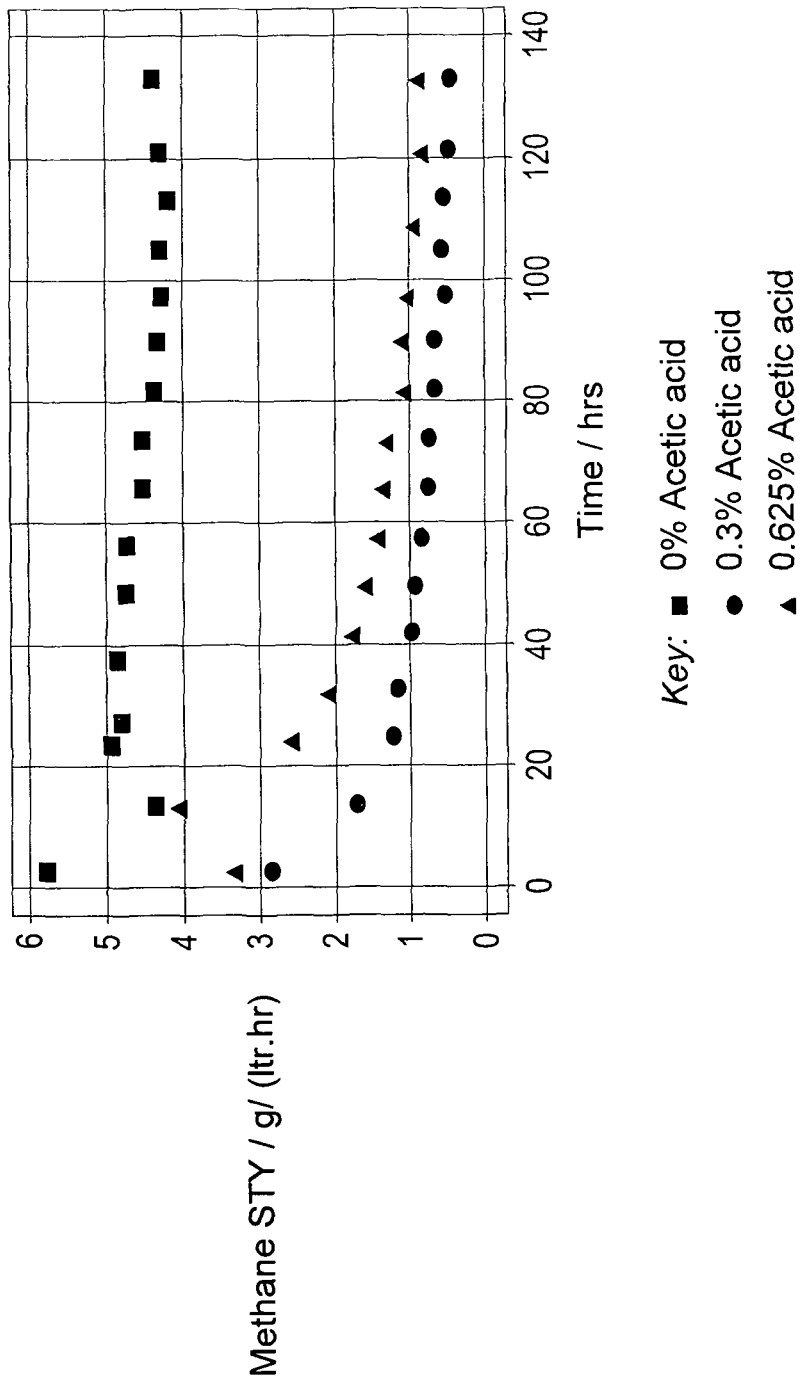

FIG. 5 depicts the space time yield (STY) to methane in g/l/hr versus time on stream for carbonylation carried out with the addition of 0 mol %, 0.3 mol % and 0.625 mol % acetic acid.

The invention is now illustrated with reference to the following Examples.

EXAMPLE 1

Carbonylation of Dimethyl Ether

This Example demonstrates the effect of employing 0 mol %, 0.05 mol %, 0.625 mol % and 2.5 mol % methyl acetate in the feed to the carbonylation of dimethyl ether with carbon monoxide in the presence of hydrogen.

Each carbonylation reaction was carried out in a pressure flow reactor unit consisting of a single hastelloy reactor. The reactor contained 55 ml glass beads, 10 ml gamma alumina and 5 ml catalyst all separated by glass wool. The catalyst consisted of a mordenite (Zeolyst CBV21A) loaded with 55 mol % copper. Prior to use the catalyst was compacted at 12 tonnes in a 26 mm die set using a pneumatic press, crushed and sieved to a pellet size fraction of 500-1000 microns. The catalyst was pressurised with helium at a flow rate of 13.2 l/h. to a reaction pressure of 30 bar and then heated to 100° C., where it was held for 17 hours. Subsequently the temperature was ramped to 300° C. at 3 deg. C./min at which point helium, carbon monoxide and hydrogen were introduced at a molar ratio of 1:4:1 (He:CO:H$_2$) to maintain a GHSV of 4000/h for 2 hours. After 2 hours, an amount of liquid dimethyl carbonate was introduced into the reactor to generate 5 mol % dimethyl ether. Where used, methyl acetate, dissolved in the dimethyl carbonate to the required amount, was also introduced into the reactor with the amount of liquid fed adjusted to maintain 5 mol % dimethyl ether. The flow rates of the helium, carbon monoxide, hydrogen, dimethyl ether and methyl acetate were sufficient to maintain a GHSV of 4000/h. Where methyl acetate was used, the helium flow was reduced to maintain the GHSV at 4000/h. The exit stream from the reactor was passed to a liquid collection vessel maintained at 20° C. which condensed the liquid products. These products were analysed at regular intervals by gas chromatography to determine the concentration of liquid reactants and liquid carbonylation reaction products. The remaining vapour stream was analysed by online GC to determine the concentration of reactants and carbonylation reaction products. The reaction was allowed to continue up to 160 hours under conditions of 300° C., 30 bar, and a gas hourly space velocity (GHSV) of 4000/h.

The results of the STY (space time yield) to methane byproduct are shown in FIG. 1. As FIG. 1 clearly shows, the presence of methyl acetate in the feed to the reaction, significantly reduces the production of methane.

EXAMPLE 2

Carbonylation of Dimethyl Ether with 1 mol % Methyl Acetate

The carbonylation of dimethyl ether in the presence of a catalyst consisting of mordenite (Zeolyst CBV21A) loaded with 55 mol % copper was carried out in a pressure flow reactor unit consisting of 16 identical reactors of the type described in WO 2005063372. Reactors with an internal diameter of 9.2 mm were employed. The centre of each reactor was fitted with internal tube of diameter 3.2 mm into which a thermocouple was placed. Prior to the loading of the catalyst into each reactor, a ca. 10 cm bed of corundum of sieve fraction of 125-160 μm was placed in the catalyst holder. On a dry mass basis (determined by loss on ignition of the catalyst measured by heating the catalyst from room temperature to 600° C. at a ramp rate of ca. 30° C. per minute) 1.948 g of catalyst (pellet size 125 to 160 microns) diluted with 3 ml of corundum (pellet size 125 to 160 microns) was placed on top of the corundum bed. Each of the zones above was concreted via hitting or vibrating to get a stable bed and a defined starting height of the catalyst zone. The diluted catalyst was covered by a ca. 13 cm corundum bed of a particle size of 125-160 μm. The catalyst was pressurised to a reaction pressure of 70 bar using a 2:1 CO:H$_2$ mixture at a flow rate of 12 l/h. The catalyst was then heated at 0.5 deg.

C./min to 220° C., where it was held for 3 hours. Subsequently the temperature was ramped to 300° C. at 0.5 deg. C./min, followed by a dwell time of 3 hours. The carbon monoxide and hydrogen feed was then switched to a mixture of carbon monoxide, hydrogen, dimethyl ether, methyl acetate, argon and nitrogen with a CO/H$_2$/dimethyl ether/Ar/methyl acetate/N$_2$ molar ratio of 54/29/2.5/5/1/8.5 at a flow rate of 12 l/h, with both dimethyl ether, at 0.30 l/h, and methyl acetate, at 0.12 l/h, fed as a vapour, to obtain a CO/H$_2$/methyl acetate/dimethyl ether ratio in the total feed of 54/29/1/2.5 on a molar basis. In addition, nitrogen gas was introduced at a variable rate of 0-150 ml/min to equalise the pressure swings between the 16 reactor exits. The exit stream from the test reactor was passed to a gas chromatograph to determine the concentration of reactants and carbonylation products. The reaction was allowed to continue for 150 hours under conditions of 300° C., 70 bar, a gas hourly space velocity (GHSV) relative to the catalyst of 4000/h with a CO/H$_2$/dimethyl ether/Ar/methyl acetate/N$_2$ molar ratio of 54/29/2.5/5/1/8.5 in the total feed.

Experiment A—Carbonylation of Dimethyl Ether in the Absence of Methyl Acetate Feed Example 2 was repeated, except that methyl acetate was not present in the feed to the carbonylation reaction. The carbonylation feed consisted of a mixture of carbon monoxide, hydrogen, dimethyl ether, argon and nitrogen with a CO/H$_2$/DME/Ar/N$_2$ molar ratio of 54/29/2.5/5/9.5 at a flow rate of 12 l/h.

The results of the carbonylation reactions of Example 2 and Experiment A are shown in FIGS. 2 to 4. The space time yield (STY) to the by-products methane and C$_{2+}$ hydrocarbons are shown in FIGS. 2 and 4 respectively. The selectivity to methyl acetate product is shown in FIG. 3.

As can clearly be seen from FIGS. 2 and 4 the presence of methyl acetate in the feed to the carbonylation reaction reduces the amount of methane and C$_{2+}$ hydrocarbons produced compared to the amount produced in the absence of methyl acetate in the reaction feed.

As can be seen from FIG. 3 the presence of methyl acetate in the feed to the carbonylation reaction provides an improved selectivity to methyl acetate product over that achieved in the absence of methyl acetate in the reaction feed.

EXAMPLE 3

Carbonylation of Dimethyl Ether with 5 mol % Methyl Acetate

The carbonylation of dimethyl ether in the presence of a catalyst consisting of mordenite (Zeolyst CBV21A) loaded with 55 mol % copper was carried out in a pressure flow reactor unit consisting of 16 identical reactors of the type described in WO 2005063372. Each reactor had an internal diameter of 3.6 mm. Prior to the loading of the catalyst into a reactor, a ca. 5 cm bed of steatite of sieve fraction of 100-350 μm was placed in the respective catalyst holder. A ca. 5 cm zone of corundum of sieve fraction of 125-160 μm was placed on top of the steatite bed. On a dry mass basis (determined by loss on ignition of the catalyst measured by heating the catalyst from room temperature to 600° C. at a ramp rate of ca. 30° C. per minute). 0.625 g of catalyst (pellet size 125 to 160 microns) was placed on top of the corundum bed. The catalyst was covered by a ca. 5 cm corundum bed of a particle size of 125-160 p.m. A ca. 5 cm zone of steatite of sieve fraction of 100-350 μm was placed on top of the corundum bed. Each zone was concreted via hitting or vibrating to get a stable bed and a defined starting height of the catalyst zone. The catalyst was pressurised to a reaction pressure of 70 bar using a 4:1 CO:H$_2$ mixture at a flow rate of 4.275 l/h. The catalyst was then heated at 0.5° C./min to a holding temperature of 220° C., where it was held for 3 hours. Subsequently the temperature was ramped to 300° C. at 0.5 deg. C./min, followed by a dwell time of 3 hours. The carbon monoxide and hydrogen feed was then changed to a CO/H$_2$/dimethyl ether feed of molar ratio 72/18/10 at a flow rate of 4.275 l/h, with a dimethyl ether vapour feed rate of 0.4275 l/h. Nitrogen gas was also introduced at a variable rate of 0-50 ml/min to equalise the pressure swings between the 16 reactor exits. The exit stream from a reactor was passed to a gas chromatograph to determine the concentration of reactants and carbonylation reaction products. The reaction was allowed to continue for 148 hours under conditions of 300° C., 70 bar, a gas hourly space velocity (GHSV) of 4275/h with a CO/H$_2$/dimethyl ether molar ratio in the total feed of 72/18/10. After 148 hours total reaction time the feed was switched to CO/H$_2$/dimethyl ether with a molar ratio of 76/19/5 and the reaction allowed to continue for a further 49 hours. After 197 hours total reaction time, a co-feed of methyl acetate was introduced to the carbonylation reactor, the reactor being fed with CO/H$_2$/dimethyl ether/methyl acetate at a molar ratio of 72/18/5/5 at 300° C., 70 bar, and gas hourly space velocity (GHSV) of 4275/h. The reaction was allowed to continue for a further 45 hours. After 242 hours total reaction time the methyl acetate co-feed was ceased, and the feed to the reactor changed to CO/H$_2$/dimethyl ether with a molar ratio of 76/19/5 at 300° C., 70 bar, and gas hourly space velocity (GHSV) of 4275/h. The reaction was allowed to continue for a further 74 hours. The results of the carbonylation reaction are given in Table 1 below.

TABLE 1

| Time/hours | DME feed/mol % | MeOAc feed/mol % | STY Methane/g l$^{-1}$ h$^{-1}$ |
|---|---|---|---|
| 194 | 5 | 0 | 6 |
| 223 | 5 | 5 | <2 |
| 288 | 5 | 0 | 6 |

Table 1 shows the results of the impact of the presence and absence of a methyl acetate co-feed on the production of methane by-product. As can clearly be seen, the presence of methyl acetate in the carbonylation feed suppresses the formation of methane and that in the absence of methyl acetate in the carbonylation feed, the production of methane increases.

EXAMPLE 4

This Example demonstrates the effect of employing 0 mol %, 0.3 mol % and 0.625 mol % acetic acid in the carbonylation of dimethyl ether. The procedure used in Example 1 was repeated except that methyl acetate was replaced by 0.3 mol % or 0.625 mol % acetic acid.

The results of the STY (space time yield) to methane by-product are shown in FIG. 5. As FIG. 5 clearly shows, the addition of acetic acid to the reaction, significantly reduces the production of methane.

The invention claimed is:

1. A process for the production of methyl acetate, which process comprises carbonylating dimethyl ether with carbon monoxide in one or more carbonylation reaction zones in the presence of a mordenite catalyst to produce methyl acetate product wherein at least one of acetic acid and additional methyl acetate is added to at least one of said reaction zone(s).

2. A process according to claim 1 wherein the process is carried out in the presence of hydrogen.

3. A process according to claim 1 wherein the molar ratio of the additional methyl acetate to dimethyl ether is in the range 1:100 to 5:1.

4. A process according to claim 3 wherein the molar ratio of the additional methyl acetate to dimethyl ether is in the range 1:10 to 3:1.

5. A process according to claim 1 wherein the additional methyl acetate is added to a reaction zone in an amount in the range 0.05 mol % to 5 mol % based on the total gaseous feeds, including recycles.

6. A process according to claim 5 wherein the additional methyl acetate is added to a reaction zone in an amount in the range 0.5 mol % to 5 mol % based on the total gaseous feeds, including recycles.

7. A process according to claim 1 wherein the additional methyl acetate is added to a reaction zone as fresh and/or recycle methyl acetate and/or as product methyl acetate.

8. A process according to claim 1 wherein the additional methyl acetate is introduced to the reaction zone on start-up of the carbonylation process.

9. A process according to claim 1 wherein acetic acid is added to a reaction zone in an amount in the range (greater than 0) mol % to 1 mol % based on the total gaseous feeds, including recycles.

10. A process according to claim 9 wherein acetic acid is added to a reaction zone in an amount in the range 0.1 mol % to 0.8 mol % based on the total gaseous feeds (including recycles).

11. A process according to claim 1 wherein the mordenite catalyst is selected from H-mordenite, a copper mordenite and a silver mordenite.

12. A process according to claim 1 wherein the process is carried out in 2 to 30 reaction zones connected in series.

13. A process according to claim 12 wherein dimethyl ether is introduced into a reaction zone as fresh and/or recycle dimethyl ether.

14. A process according to claim 13 wherein dimethyl ether is introduced to a reaction zone as fresh dimethyl ether together with at least one of fresh and/or recycle methyl acetate and acetic acid.

15. A process according to claim 1 wherein methyl acetate product is hydrolysed to acetic acid.

16. A process according to claim 1 wherein the carbon monoxide is fed into a reaction zone as a mixture with hydrogen.

17. A process according to claim 16 wherein the carbon monoxide and hydrogen are present in the mixture in a molar ratio of 1:3 to 15:1.

* * * * *